US008355482B2

(12) United States Patent
Brown et al.

(10) Patent No.: US 8,355,482 B2
(45) Date of Patent: Jan. 15, 2013

(54) RADIOTHERAPY APPARATUS

(75) Inventors: Kevin Brown, Horsham (GB); Maria Giulia Thompson, Redhill (GB); Vibeke Nordmark Hansen, Sutton (GB); Philip Mark Evans, Sutton (GB); David Anthony Roberts, London (GB)

(73) Assignee: Elekta AB (publ), Stockholm (SE)

( * ) Notice: Subject to any disclaimer, the term of this patent is extended or adjusted under 35 U.S.C. 154(b) by 129 days.

(21) Appl. No.: 12/992,727

(22) PCT Filed: May 15, 2009

(86) PCT No.: PCT/GB2009/001217
§ 371 (c)(1),
(2), (4) Date: Nov. 15, 2010

(87) PCT Pub. No.: WO2009/138753
PCT Pub. Date: Nov. 19, 2009

(65) Prior Publication Data
US 2011/0142202 A1 Jun. 16, 2011

(30) Foreign Application Priority Data
May 16, 2008 (GB) .................................. 0808973.2

(51) Int. Cl.
*A61N 5/10* (2006.01)
*H01J 35/08* (2006.01)
*G21K 3/00* (2006.01)
(52) U.S. Cl. ........................... 378/65; 378/124; 378/156
(58) Field of Classification Search ................ 378/4, 19, 378/62, 64, 65, 124, 119
See application file for complete search history.

(56) References Cited

U.S. PATENT DOCUMENTS
3,925,660 A 12/1975 Albert
(Continued)

FOREIGN PATENT DOCUMENTS
EP 1498908 A2 7/2004
(Continued)

OTHER PUBLICATIONS
Kajzar, Anna, International Search Report and Written Opinion; PCT/GB2009/001217, Feb. 11, 2009.
(Continued)

*Primary Examiner* — Irakli Kiknadze
(74) *Attorney, Agent, or Firm* — Sunstein Kahn Murphy & Timbers LLP

(57) ABSTRACT

It is desirable to achieve a co-incident investigative kV source for a therapeutic MV source—a so-called "beams-eye-view" source. It has been suggested that bremsstrahlung radiation from an electron window be employed; we propose a practical structure for achieving this which can switch easily between a therapeutic beam and a beam-eye-view diagnostic beam capable of offering good image resolution. Such a radiation source comprises an electron gun, a pair of targets locatable in the path of a beam produced by the electron gun, one target of the pair being of a material with a lower atomic number than the other, and an electron absorber insertable into and withdrawable from the path of the beam. In a preferred form, the electron gun is within a vacuum chamber, and the pair of targets are located at a boundary of the vacuum chamber. The lower atomic number target can be Nickel and the higher atomic number target Copper and/or Tungsten. The electron absorber can be Carbon, and can be located within the primary collimator, or within one of a plurality of primary collimators interchangeably locatable in the path of the beam. Such a radiation source can be included within a radiotherapy apparatus, to which the present invention further relates. A flat panel imaging device for this source can be optimised for low energy x-rays rather than high energy; Caesium Iodide-based panels are therefore suitable.

20 Claims, 9 Drawing Sheets

U.S. PATENT DOCUMENTS

| | | | |
|---|---|---|---|
| 3,969,629 A | 7/1976 | McIntyre |
| 4,121,109 A | 10/1978 | Taumann |
| 4,352,021 A | 9/1982 | Boyd |
| 4,760,590 A | 7/1988 | Azam |
| 5,471,516 A | 11/1995 | Nunan |
| 5,757,881 A | 5/1998 | Hughes |
| 6,445,766 B1 | 9/2002 | Whitman |
| 6,618,466 B1 | 9/2003 | Ning |
| 2002/0122531 A1 | 9/2002 | Whitham |
| 2005/0123097 A1 | 6/2005 | Wang |
| 2007/0018117 A1 | 1/2007 | Calderon |

FOREIGN PATENT DOCUMENTS

| | | |
|---|---|---|
| EP | 1498908 A3 | 1/2005 |
| EP | 1595500 A1 | 11/2005 |
| WO | 2005037074 A2 | 4/2005 |
| WO | 2006130630 A2 | 12/2006 |
| WO | 2006130630 A3 | 4/2007 |
| WO | 2005037074 A3 | 4/2009 |

OTHER PUBLICATIONS

Stransom, Alison, International Search Report, GB0808973.2, Aug. 27, 2008.

RADIOTHERAPY APPARATUS

FIELD OF THE INVENTION

The present invention relates to radiotherapy apparatus.

BACKGROUND ART

The accurate delivery of radiotherapy to a patient depends on a number of factors, including the accurate determination of the patient's current position, in terms of both their gross external position and the position of the internal structures that are to be irradiated or avoided. Some form of investigative x-ray apparatus is therefore a valuable part of a radiotherapy apparatus.

Given that the apparatus itself is capable of producing a beam of x-rays, it might be thought that this could be used as an investigative source. However, the therapeutic beam is typically at a high energy (in the MV range) and therefore the image contrast is poor and the dose delivered to the patient is relatively high. The poor contrast results from the attenuation coefficients that apply at higher energies as opposed to those that apply, at lower energies. At higher energies, the coefficients of bone and tissue are similar, thereby limiting the potential contrast that is obtainable.

It is therefore desirable to use a lower energy beam for investigative purposes. Beams with energies in the kV range can be detected more easily, apply a lower dose to the patient, and interact mainly via the photoelectric effect. The latter effect is dependent on atomic number, and the large difference between bone (20Ca) and water (1H and 8O) therefore allows a much better image contrast.

However, a separate source of kV x-rays presents various engineering difficulties. Such a source inherently adds additional cost and complexity to the apparatus. Further, spatial clearance requirements dictate that such sources view the patient along an axis that is offset by 90° from the therapeutic beam axis. Thus, as the therapeutic source is rotated around the patient, the diagnostic source is likewise rotated. These axes need to be aligned, and need to be kept in alignment.

It is therefore desirable to achieve a co-incident investigative kV source for a therapeutic MV source—a so-called "beams-eye-view" source. However, this is not a trivial step.

Galbraith ("Low-energy imaging with high-energy bremsstrahlung beams", Medical Physics Vol. 16 No. 5, September/October 1989 pp 734-746) reported that simple replacement of the Tungsten or Copper target with a low-Z Carbon or Beryllium target allowed the production of a low-energy beam which could be used for diagnosis. Galbraith also noted that the electron beam will interact with the electron window to produce bremsstrahlung radiation which he was able to use for imaging. Accelerators typically operate by producing a high-energy beam of electrons; this is allowed to impinge on a target to produce x-rays. The electron beam moves from its vacuum enclosure to the atmosphere via an "electron window" in the enclosure, of Aluminium in Galbraith's case. Galbraith noted that in doing so, the beam produced x-radiation. Normally, this would be absorbed by the conventional treatment target, but without a target it is free for use in diagnosis.

Galbraith's suggestion of the electron window as a target also left the hypothetical patient being irradiated with the main part of the electron beam. Galbraith concluded that manufacturers should incorporate diagnostic modes in future accelerators to allow for modification in this direction, as the application of the method to standard accelerators "would in general be a difficult task".

Flampouri et al. ("Optimisation of megavoltage beam and detector characteristics for portal imaging in radiotherapy", PhD thesis, University of London, 2003) demonstrated the replacement of the conventional Tungsten or Copper target for an MV source with an aluminium target and the removal of the conventional flattening filter, to produce a low energy beam from the apparatus otherwise used to produce an MV beam suitable for imaging, including projection radiographs and CT imaging using the treatment machine.

Zheng et al ("Simple Beamline Modifications for High Performance Portal Imaging", 8th International Workshop on Electronic Portal Imaging, Brighton, UK, 29th Jun. to 1 Jul. 2004) reported the replacement of the conventional Tungsten or Copper target for an MV source with a graphite or aluminium target and the removal of the conventional flattening filter, to produce a low energy beam from the apparatus otherwise used to produce an MV beam.

To allow for interchangeability of the target, however, the cassette carrying the standard and graphite or aluminium targets is located outside the vacuum enclosure, and therefore some distance from the source. Zheng does not discuss any interaction between the electron beam and the window, although he references Galbraith.

SUMMARY OF THE INVENTION

The prior art described in the previous section is either concerned with the production of X-rays from the vacuum window suitable for imaging during electron therapy [Galbraith] or with the use of low-Z targets on which electrons impinge to produce X-rays suitable for imaging [Galbraith, Flampouri, Zheng].

To date, therefore, there does not appear to be a device able to switch easily between a therapeutic beam and a beam-eye-view diagnostic beam produced by the vacuum window and is therefore capable of offering good image resolution, high contrast images and low patient dose.

The x-ray production method described herein consists of a thin electron/vacuum window, which acts as an X-ray transmission target for impinging electrons, combined with an electron beam absorber of lower atomic number than the material of the vacuum window. The electron window transmits a large proportion of the electron beam but is of a sufficient thickness that on average a relatively small proportion of the electrons energy is deposited and converted to useful bremsstrahlung radiation suitable for imaging applications. This is in contrast to a conventional imaging or therapy target, where all electrons are absorbed within the target. The lower atomic number electron beam absorber serves to remove the residual electrons transmitted through the vacuum window (which otherwise would result in unacceptable levels of patient skin dose). In addition, depending on the X-ray spectrum produced, a diagnostic filter can be included to reduce the skin dose by removing X-rays of energy approximately <30 keV.

The present invention therefore provides a radiation source, comprising an electron gun, a pair of targets locatable in the path of a beam produced by the electron gun, the targets having different emission characteristics, and an electron absorber insertable into and withdrawable from the path of the beam. Generally, one of the targets will be thin and will also act as the vacuum window. In this way, a practical and realisable device is provided which is able to employ the principle of using the vacuum window for imaging enumerated by Galbraith in a manner that is safe and practical to use with patients. In the described embodiment, the targets are interchangeably locatable in the path, but other designs of radiation source may differ.

In the current Elekta design, the electron gun is within an evacuated region and the therapy target is located in a wall portion of the vacuum chamber. Electrons accelerated by the gun impinge on the target and produce an x-ray beam outside the chamber. To move the apparatus out of its "therapy x-ray" mode into its "electron" mode, the target is moved to one side, out of the electron beam, and a Nickel electron window moves into position. We therefore propose to use the electron/vacuum window as an imaging target; therefore, in a preferred form of the present invention the electron gun is within a vacuum chamber, and the pair of targets are located at a boundary of the vacuum chamber.

Thus, one target (imaging target/vacuum window) is preferably of Nickel or other suitable material (e.g. stainless steel, titanium), that can be formed into a relatively thin target, able to withstand the electron beam current, to act as a vacuum/air interface and of sufficient thickness to produce bremsstrahlung radiation but thin enough to transmit the bremsstrahlung photons so as not to be self absorbing. Such a target is capable of acting as an electron window (where desired) to allow the apparatus to produce a therapeutic electron beam. However, the atomic number properties of Nickel or other suitable material formed into a thin target will allow the production of a useful bremsstrahlung radiation. The other target (therapy target) can be a conventional x-ray target such as at least one of Copper, Tungsten, or a composite including Copper and Tungsten. The electron absorber, which is located outside the vacuum chamber and is used in conjunction with the imaging target only, preferably comprises a material of atomic number lower than the vacuum window, such as Carbon, Beryllium, Aluminium etc. In addition, the use of a diagnostic filter made of Aluminium or other suitable material can be included to reduce the skin dose in imaging mode.

Most radiation sources of this type include a primary collimator, located in the beam subsequent to the targets. The electron absorber/insert can be located in the primary collimator or any other location suitably close to the vacuum window. Our current design includes a pair of alternative primary collimators, one associated with the x-ray therapy target and another associates with the Nickel electron window. We therefore prefer that there are a plurality of primary collimators interchangeably locatable in the path of the beam, at least one of which primary collimators contains the electron absorber.

Such a radiation source can of course be included within a radiotherapy apparatus, to which the present invention further relates. In such apparatus, the radiation source is usually rotatable around a horizontal axis that lies in the path of the beam, a horizontal axis that is usually perpendicular to the beam. We prefer that there is also an electronic imaging system in the path of the beam, and (more preferably) a patient support between the source and the electronic imaging system. The latter may incorporate a flat panel imaging device, which can be optimised for a low energy x-ray source rather than the high energy for which a panel in this location is usually optimised. Panels based on scintillator crystals are therefore suitable. Current panels are based on Caesium Iodide, Gadolinium Oxisulphide or Cadmium Tungstate, but others may become available.

Thus, preferred embodiments of the x-ray production method described herein consist of a thin vacuum window, which acts as an X-ray transmission target for impinging electrons, combined with an electron beam absorber of lower atomic number than the material of the vacuum window; the thin vacuum window produces a photon beam of energy suitable for imaging applications and the electron beam absorber serves to remove the electrons transmitted through the vacuum window (which otherwise would results in unacceptable levels of patient skin dose). In addition, depending on the X-ray spectrum produced, a diagnostic filter can be included to reduce the skin dose by removing X-rays of energy approximately <30 keV.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
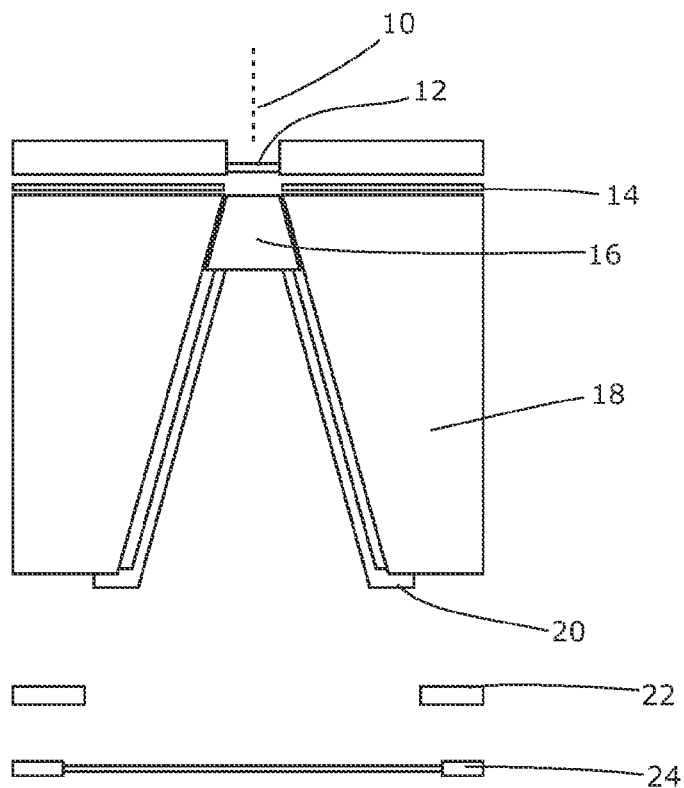
FIG. 1 shows a schematic diagram of the top section of the experimental low Z setup. The primary scatter foil assembly is at the hole/photon position and the secondary filter carousel is empty.

The successful treatment of cancer with radiotherapy requires a large radiation dose to be deposited accurately in both position and intensity. To verify that the patient is in the correct position, portal images have traditionally been acquired throughout the patient's treatment. These images are produced using the megavoltage treatment beam and (unfortunately) suffer from inherently low contrast. This in turn limits the ability to position the patient accurately. An increase in accuracy could potentially lead to higher tumour control and/or lower normal tissue complication with the expectation of improved therapeutic benefit.

Several methods for improving this situation have been proposed and fall into three categories. The first method involves changing the object properties, for example by inserting fiducial markers in the treatment region. Secondly, improvements to the imaging device can be made, and thirdly the imaging beam spectrum may be modified. The latter either involves attaching a kV source to the linac, integrating a kV source in the linac or introducing lower atomic number (Z) targets into a standard linac. In the last three cases the aim is to produce an imaging spectrum with a high proportion of photons between the energies of 40 and 200 keV. At these energies, the photo-electric interaction dominates, and thus bone and soft-tissue contrast is increased compared to standard MV images where Compton scatter dominates.

This invention is based on employing a thin electron/vacuum window to act as an X-ray transmission target for impinging electrons, combined with an electron beam absorber of lower atomic number than the material of the vacuum window and possibly a diagnostic filter. This arrangement results in bremsstrahlung production with a significantly lower average energy than the treatment beam. The use of a thin, high Z detector can be used to image the lower energy section of the linac spectrum. It involves an arrangement of a linear accelerator for CT imaging using a beam modified to improve image quality by a combination of lowering the beam energy, modifying the x-ray target, and using the components of the linear accelerator to shape the beam and optimising a detector to image the beam.

The implementation of a beam's-eye-view imaging system differs across the literature. Galbraith (1989) primarily used experimental techniques to produce high contrast images of thin objects using a thick low Z target. The images were acquired using film sensitive to energies in the diagnostic range. Ostapiak et al. (1998) and Tsechanski et al. (1998) investigated adjusting the thickness and composition of targets using Monte Carlo methods. They did not however investigate the full imaging system with Monte Carlo methods as in Flampouri et al. (2002). Flampouri et al. (2002) deduced the optimal target to be 6 mm of aluminium whilst Tsechanski et al. (1998) used 1.5 mm of copper. All the previous studies differ in the way the system was implemented. Of particular note is that different linac types and models were used in each study, which subsequently affected the positioning of the low Z target. Galbraith (1989) and Ostapiak et al. (1998) placed their targets as close to the electron window as possible, whilst Flampouri et al. (2002) and Tsechanski et al. (1998) placed the targets in the secondary filter carousel.

Experimental Arrangement

We have developed an optimum design for an imaging beam given that the lower-Z absorber should be placed as close as possible to the vacuum window, without a major re-design of the linac head.

An Elekta Limited Precise™ treatment system linac (Elekta Limited, Crawley, UK) was modified by placing a low Z insert into the high energy collimator port. The insert consisted of 2 cm of carbon (density=1.8 g·cm-3) supported by an aluminium alloy cone that fixed to the high energy difference filter mountings on the bottom of the primary collimator. The thickness of the carbon insert was sufficient to stop all primary electrons emerging from the electron window. The carbon insert was placed in the primary collimator as this was the closest position it could be placed to the exit window of the waveguide.

The linac was operated in 4 MeV electron mode with the primary and secondary scatter foils removed. The only items in the beam path were the nickel electron window, carbon insert, monitor ion chamber, mirror and Mylar cross hair sheet. To increase the dose rate from the linac the electron gun current was increased to match the current used in the high dose rate electron (HDRE) mode of the linac. This increases the beam current by a factor of 10, enabling images to be acquired in clinically acceptable times (circa 1 second). This beam current was used as linacs of this model had previously been life tested to this level.

A schematic diagram of the top section of the linac (excluding Jaws and Multi-leaf collimator) can be seen in FIG. 1. This includes an electron path 10 leading to a Nickel electron window 12. After the primary scatter foil assembly 14, the resulting beam meets a 2 cm carbon filter/absorber 16 mounted in one of the rotatable primary collimators 18. The carbon filter/absorber 16 is supported in place by an aluminium holder 20 attached to the primary collimator 18. Below the primary collimator 18 is the secondary filter carousel 22 and then the ion chamber 24.

Additional filters may also be placed, including the imaging bowtie filter (usually present in CT scanners to correct for beam intensity variations arising from patient geometry) and the use of collimators to shape the beam. These may be the normal collimation system of the treatment machine, such as multileaf collimators or conventional jaw collimators. The position of the electron absorber may be at one of various distances from the electron window, but is best placed close to the electron window to maintain a small focal spot and hence high spatial resolution.

A tissue-equivalent phantom, Atlantis (Flampouri et al. 2002) was used as a quantitative measure of contrast of the different x-ray systems. The phantom consists of varying thicknesses of bone equivalent plastic surrounded by water. Three water depths were used; 5.8, 15.8 and 25.8 cm, so as to estimate contrast in the head and neck, torso, and pelvis respectively. The water depths are made up of 0.8 cm Perspex (density=1.03 g·cm-3) and the remainder is water e.g. 5.8 cm=5 cm water+0.8 cm Perspex. The spatial resolution of the system was assessed by analysing a PIPS pro phantom (Rajapakshe 1996) and images acquired of a humanoid anthropomorphic phantom for the head and neck for qualitative image assessment.

Figure 2:
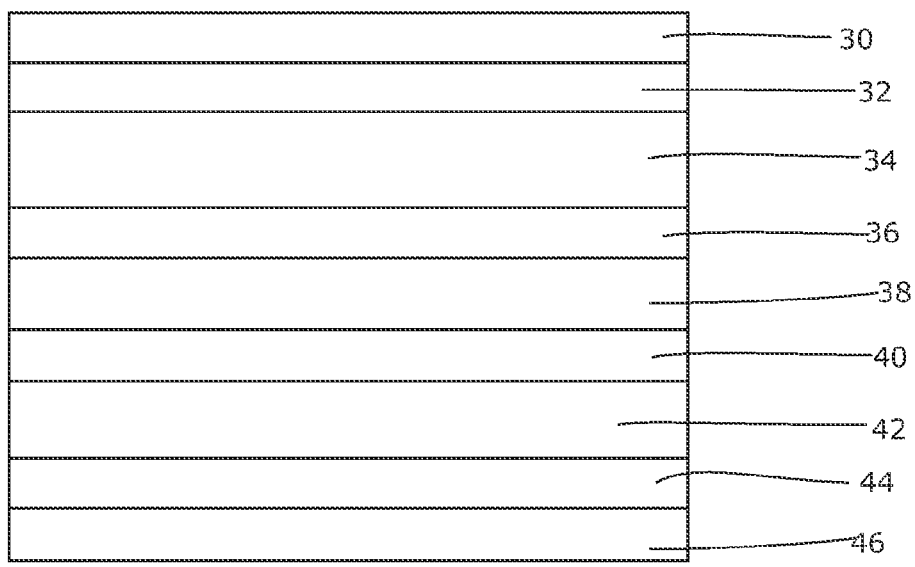
FIG. 2 shows the detector layers of an iViewGT.

Two in-direct amorphous silicon based detectors (Antonuk 2002) manufactured by PerkinElmer (Fremont, Calif., USA) were employed. The Elekta iViewGT electronic portal imager (EPID) and the Elekta XVI panel were also considered. The basic detector layers can be seen in FIG. 2 (which is not to scale) for the iViewGT panel (Parent et al. 2006). These are:

The major difference between the XVI panel and the iViewGT panel is the omission of the copper plate and the substitution of the gadolinium oxisulphide scintillator for a columnar, thallium doped, Caesium Iodide (CsI(Th)) crystal. The iViewGT panel is normally used for imaging the megavoltage linac beam and the XVI panel is currently used on the Elekta Synergy system for imaging with kV photons.

All panels were positioned in a standard megavoltage detector arm, resulting in a distance of 159 cm from the target to the panel surface. Images were acquired using the PerkinElmer x-ray imaging software (XIS) and the panels ran in free running mode i.e. not synchronized to the beam delivery. The iViewGT panel acquired images at 568 ms and the XVI panel at 142.5 ms. Both frame rates where chosen to avoid saturating the detectors during open field acquisitions, but to also give good dynamic range. All images were offset and gain corrected using equation 1 on a pixel by pixel basis. $I_{corrected}$ is the gain and offset corrected image, $I_{measured}$ IS the image to be corrected, $I_{gain}$ is a 26×26 cm open field image and $I_{offset}$ is an image acquired when the panel is not being irradiated.

$$I_{corrected}(x, y) = \frac{I_{measured}(x, y) - I_{offset}(x, y)}{I_{gain}(x, y) - I_{offset}(x, y)} \quad (1)$$

The Low Z linac was characterised by obtaining depth dose curves and profiles in a water tank (Scanditronix-Wellhofer)

using a CU500E controller unit and electrometer. The field and reference chambers were compact cylindrical ion chambers, type CC13 with a 0.13 cc sensitive volume (Scanditronix-Wellhofer). Depth dose curves and profiles were acquired for a 20×20 cm field, SSD=95 cm for both the 6MV and low Z beam using both Monte Carlo and experimental measurements.

The two detectors described previously were modelled using DOSXYZnrc. A previously published model of the iViewGT panel was used (Parent et al. 2006). This was modified for the XVI panel i.e. removal of copper plate and modification of scintillator type and thickness. The image was taken as the dose deposited in the scintillator. Optical photon transport was not included as it was not expected to affect image properties in this case (Evans et al. 2006).

To investigate the response of the panels to various input x-ray spectra the dose deposited in the scintillator layer of the detectors was simulated for various mono-energetic pencil beams. These beams were evenly spaced on a log 10 scale between 0.001 MeV and 10 MeV so as to sample adequately the response of the detectors over the range of energies in question.

The contrast was calculated by analysing the average pixel value in each of the bone segments and using equation 2. I0cmbone is the average pixel intensity in the section of the Atlantis phantom with no bone insert (0 cm) and Ixcmbone, is the average pixel intensity in the section of the Atlantis phantom with an x cm bone insert. To negate errors associated with a tilted beam and to account for the un-flattened nature of the low Z beam, images of the Atlantis phantom where 'flattened' by dividing this image by one of the same water thickness but without the bone inserts.

$$Contrast_{xcmbone} = \frac{I_{0cmbone} - I_{xcmbone}}{0.5 * (I_{0cmbone} + I_{xcmbone})} \quad (2)$$

Figure 3:
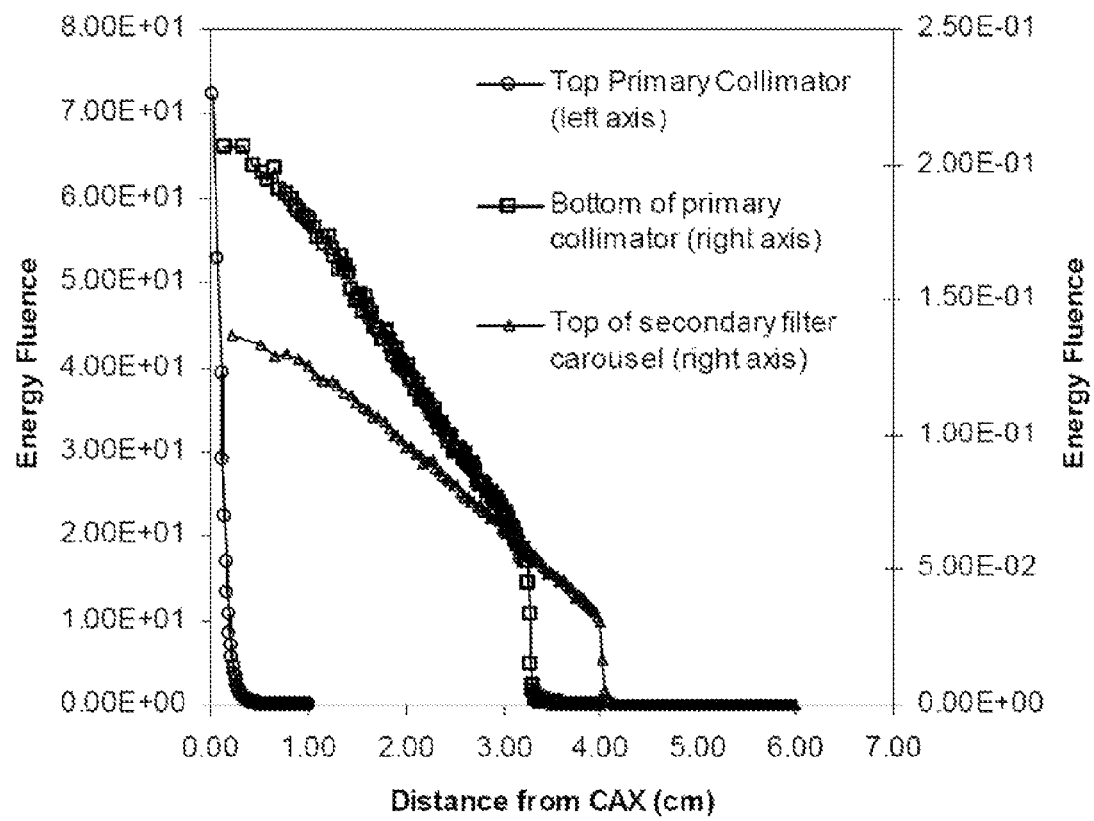
FIG. 3 shows the electron energy fluence at various stages of the low Z linac.

FIG. 3 shows the results of Monte Carlo calculation of the electron energy fluence at various levels in a linac for 4 MeV electrons. It can be seen that shown that the electrons scatter substantially in air between the electron window and the secondary filter carousel. The electron fluence distribution is 8 cm wide at the secondary filter carousel and thus any image formed with a target at this level would suffer severe spatial resolution degradation. Therefore, to obtain high resolution images the absorber cannot be placed far from the vacuum window.

Figure 4:
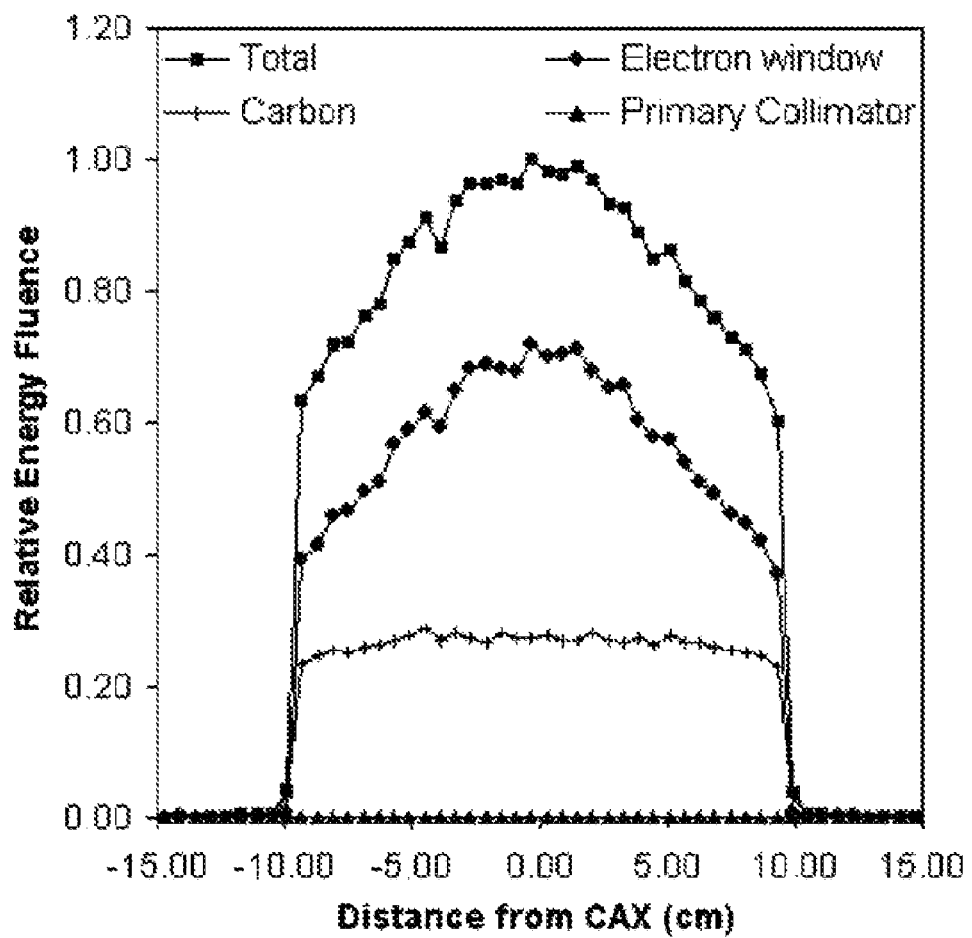
FIG. 4 shows the energy fluence components at SSD=100 cm for Low Z linac with a 20×20 cm field.

The Monte Carlo model of the low Z linac shows a substantial photon fluence from the Nickel electron window. FIG. 4 shows that at the isocentre plane, 71% of the photon fluence is from primary photons produced in the nickel window. Table 1 shows the proportions in the central 5×5 cm of a 20×20 cm field.

TABLE 1

Energy Fluence contributions in a 5 × 5 cm square at SSD = 100 cm for the Low Z linac with a 20 × 20 cm field

| Component | % of photon energy fluence |
| --- | --- |
| Ni electron window | 70.95 |
| Primary Collimator | 0.7 |
| Carbon absorber | 28.23 |
| Other | Remainder (0.12) |

Galbraith (1989) deliberately formed images using photons produced from an aluminium electron window in an AECL Therac-20 accelerator, but the contribution from such photons was not discussed in subsequent low Z papers (Flampouri et al. 2002, Ostapiak et al. 1998, Tsechanski 1998). The production of a significant photon fluence in the thin nickel window arises due to nickel's high atomic number (Z=28) and density (8.9 g·cm-3). As bremsstrahlung production is proportional to Z2, the efficiency of the process is greatly increased for the high Z, nickel window over the low Z, carbon insert.

In our design the Carbon absorber acts primarily to remove primary electrons from the beam; as a by-product it also produces further low energy bremsstrahlung photons. It must be noted that the proportion of photons from the electron window will depend on the type of the linac used due to a variety of different materials and thicknesses being used by the linac manufacturer.

Figure 5:
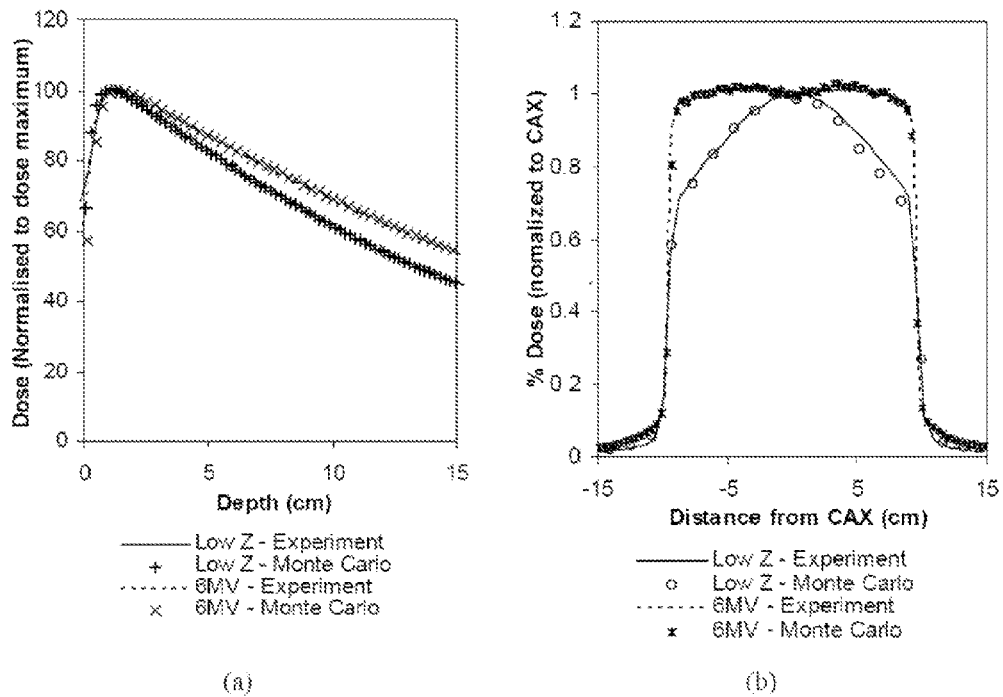
FIG. 5(a) shows depth dose curves for the low Z and 6MV Beam for a 20×20 cm field, and 5(b) shows profiles at 1 cm deep, SSD=95 cm for the low Z beam with a 20×20 cm field size.

FIGS. 5a and 5b show the depth dose curves and profiles for the low Z beam for the Monte Carlo simulations and experiment. Good agreement is seen between the Monte Carlo and experimental results suggesting that the model of the system is accurate. A slight tilt in the experimental beam is present as shown in FIG. 5b, and this is likely due to a small tilt in the carbon insert or due to the non-standard operating mode of the ion chamber and servo system. The latter is affected by the lack of secondary electrons normally generated in the flattening filter. This results in a lack of electronic equilibrium in the ion chamber. 6MV data is also shown highlighting the different dosimetric properties of the beams. For 20×20 cm fields the 6MV beam $d_{max}$ is at 1.25 cm whilst it is 1.15 cm for the Low Z beam.

Figure 6:
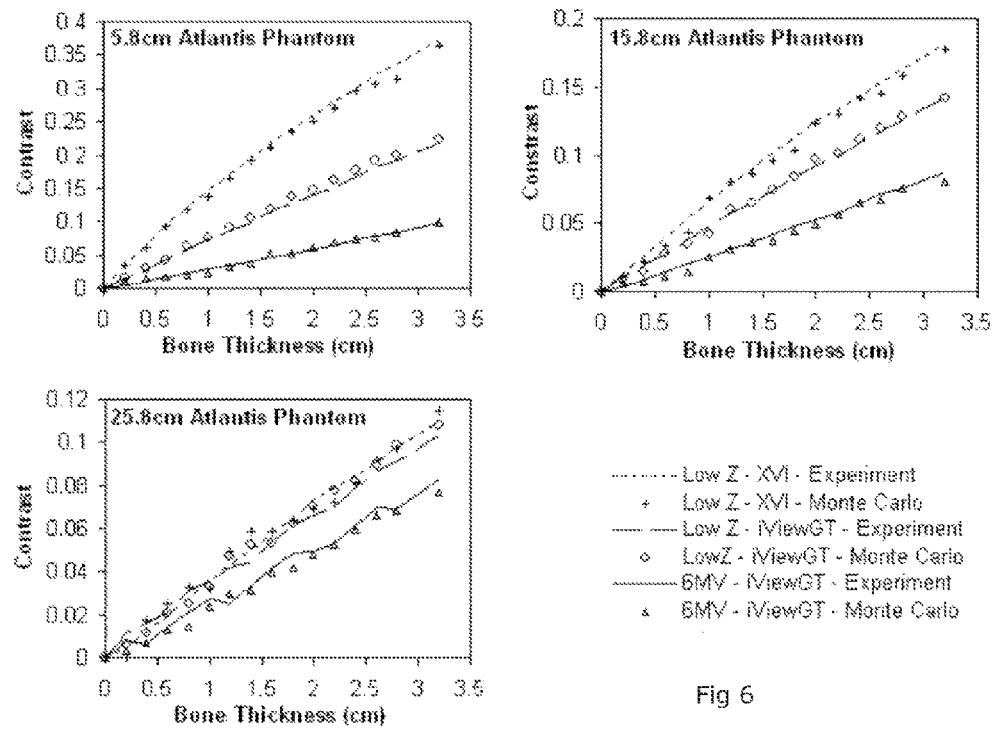
FIG. 6 shows inherent contrast levels for the LowZ/XVI and 6MV/iViewGT combinations.
Figure 7:
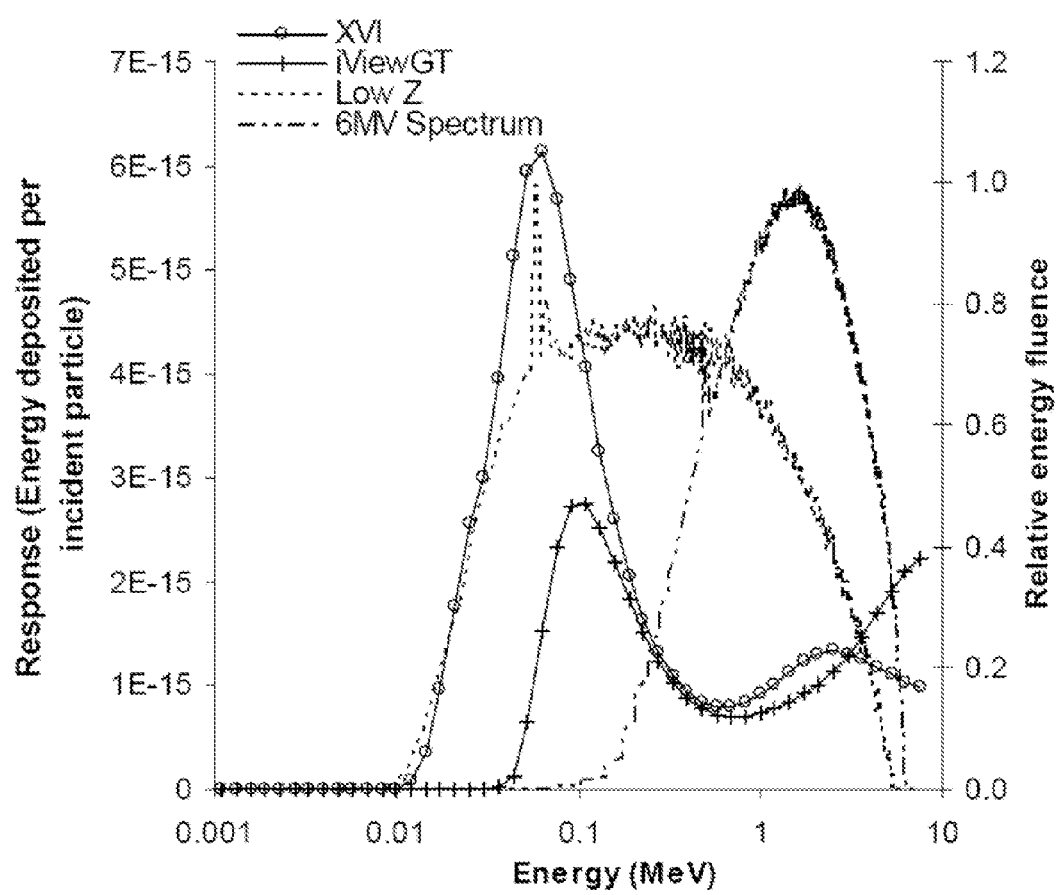
FIG. 7 shows response curves for the XVI and iViewGT panels and photon spectra for the 6MV and low Z beams.

Inherent contrast results calculated for the Atlantis phantom are shown in FIG. 6. Significant improvements in contrast are seen for all low Z beam systems over the standard 6MV/iViewGT system. For thin, 5.8 cm phantoms contrast for 1.6 cm bone increases by a factor of 2.42 with the LowZ/iViewGT system and by a factor of 4.62 with the LowZ/XVI setup. For thicker phantoms the improvement in contrast decreases but even with a 25.8 cm phantom a 1.3 times increase in contrast is noted with the low Z beam. The increase in contrast is due to two factors. Firstly the low Z linac produces a higher proportion of diagnostic x-rays than the 6MV linac and secondly that the different panels are sensitive to different regions of the photon spectrum. FIG. 7 illustrates the response of the different detectors as well as the different photon spectra produced by the low Z and 6MV linacs.

At energies around the mean of the 6MV beam (1.6 MeV), the response of all detectors is very low whilst there are very few photons around 100 keV for the 6MV beam. Conversely the un-attenuated low Z beam has its peak fluence at or around the maximum response of the detectors. The Elekta iViewGT is less responsive than the XVI panel, owing to the thinner and hence less quantum efficient scintillator. The copper plate also limits the quantity of low energy photons that reach the scintillator.

Due to the megavoltage nature of the low Z beam significant beam hardening occurs for thick phantoms. As the phantoms get thicker the beams are stripped of the low energy photons resulting in lower contrast images. This observation of very little contrast improvement for thicker phantoms has been noted previously (Flampouri et al. 2002, Galbraith 1989, Ostapiak 1998, Tsechanski 1998) and is therefore an inherent disadvantage of any megavoltage generated low Z beam.

Table 2 presents the dose needed to form an image with the same Signal to noise ratio as the conventional 6MV/iViewGT system. The contrast value quoted is for 1.6 cm Bone in x cm water. Table 3 shows the imaging dose required to form an image with the same Contrast to Noise Ratio (CNR).

TABLE 2

Dose comparison for the low Z/XVI system when the SNR is kept the same as the standard 6MV/iViewGT system.

| Phantom | Beam | SNR | Dose | % of 6MV Dose | Contrast |
|---------|------|-----|------|---------------|----------|
| 5.8 cm water | 6MV/iViewGT | 96.35 | 2cGy | 100% | 0.0474 |
|  | LowZ/XVI | 96.35 | 0.1325cGy | 6.63% | 0.2190 |
| 25.8 cm Water | 6MV/iViewGT | 68.89 | 2cGy | 100% | 0.0426 |
|  | LowZ/XVI | 68.89 | 0.4819cGy | 24% | 0.0575 |

TABLE 3

Dose comparison at a constant contrast to noise ratio.

| Phantom | Beam | CNR | Dose | % of 6MV Dose |
|---------|------|-----|------|---------------|
| 5.8 cm water | 6MV/iViewGT | 21.39 | 2cGy | 100% |
|  | LowZ/XVI | 21.39 | 0.00901cGy | 0.45% |
| 25.8 cm Water | 6MV/iViewGT | 8.3704 | 2cGy | 100% |
|  | LowZ/XVI | 8.3704 | 0.272cGy | 13.6% |

Both sets of results show a significant dose saving for thin phantoms. A dose reduction of a factor of 14 is possible for a 5.8 cm phantom whilst still obtaining a 4.62 times increase in contrast. For the thickest phantom a dose saving of a factor of 3 and an increase in contrast of a factor of 1.3 is observed. Contrast to noise ratio calculations show that a further reduction in dose is possible for constant CNR. 0.5% of the dose is required for thin phantoms for the low Z beam compared to the 6MV system. For thicker phantoms we still require only 13.6% of the dose of the 6MV images for the Low Z system.

Imaging times vary according to the phantom thickness due to the restricted beam current used for the low Z beam, to safeguard the electron window. For a 5.8 cm phantom, images with the same SNR as a 2cGy 6MV image can be acquired in 0.35 seconds. For a 25.8 cm phantom this increases to 1.27 seconds. These times are acceptable for portal imaging, but if quicker acquisitions were required for cone beam CT then the SNR would have to be sacrificed or a thicker scintillator with a high quantum efficiency (QE) employed.

Figure 8:
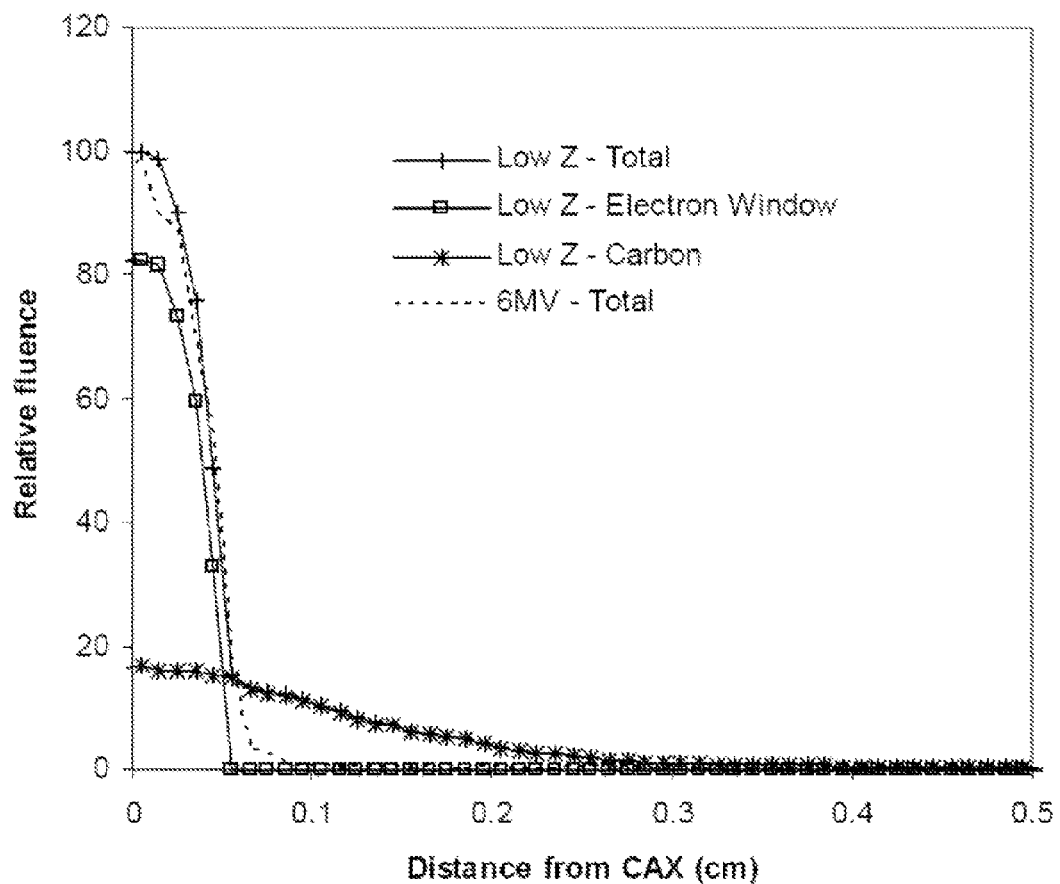
FIG. 8 shows a Monte Carlo calculated source size for 6MV and Low Z setups.
Figure 9:
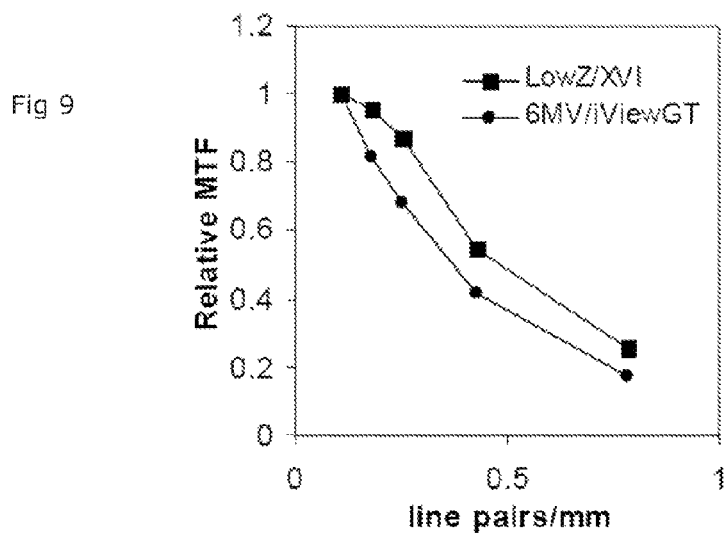
FIG. 9 shows MTF results for 6MV/iViewGT and Carbon/XVI.
Figure 10:
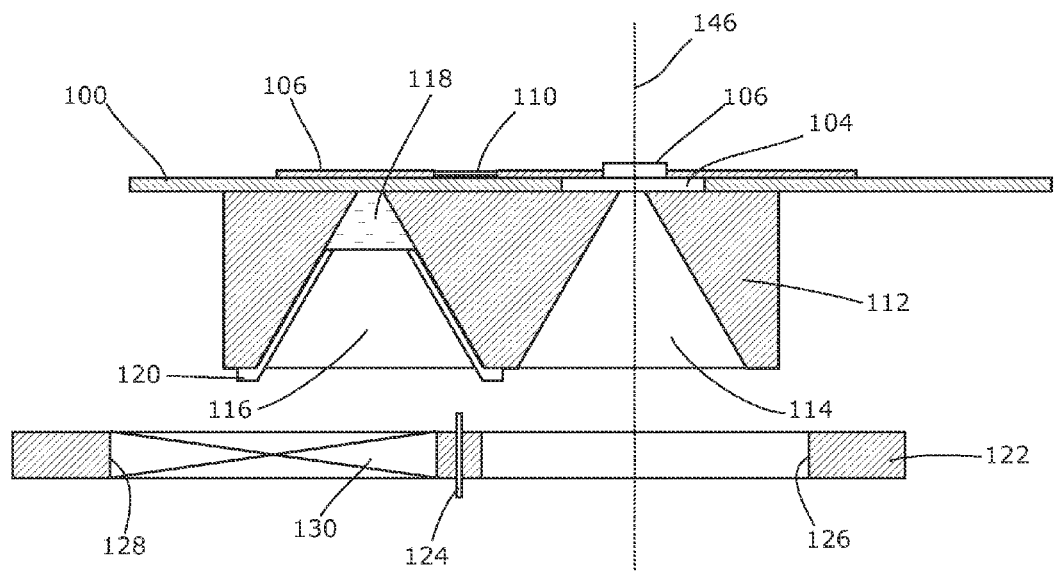
FIG. 10 shows the region around the target & primary collimator of a practical embodiment, in a first arrangement.

We also considered the spatial resolution that is achievable. The photon source of the low Z linac is a combination of photons emitted from the electron window and Carbon insert as shown in FIG. 8. For both the 6MV and low Z Monte Carlo simulations, the input electron spot size was the same. However due to the different positions of the targets the overall photon spot shape is slightly different. The 50% points are similar for the two systems but the Low Z beam has a broader tail around the 15% region. The broadening of the tails is due to the larger electron spot hitting the Carbon insert after passing through the nickel electron window and being scattered in a volume of air. This could be improved by moving the carbon insert/absorber closer to the nickel window. The spatial resolution of the whole system was assessed by measuring the MTF using the PIPS-pro phantom placed on a couch at SSD=105.8 cm. FIG. 9 shows the MTF's for the LowZ/XVI and 6MV/iViewGT systems.

The LowZ/XVI system therefore performs better at higher frequencies resulting in sharper images. Whilst the detectors are similar, the presence of the copper plate on the iViewGT panel increases the size of the point spread function for the 6MV beam by scattering electrons and photons before they interact with the scintillator. Also the higher energy 6MV photons may scatter larger distances and can backscatter into the scintillator. On the other hand the secondary source of photons from the carbon insert in the low Z linac act to reduce the MTF as they broaden the low Z spot size.

Analysis of the results of qualitative Phantoms showed that image quality is superior in the Low Z/XVI image, supporting the quantitative measurements described previously despite the image being formed with a lower dose. Teeth, oral cavity and spine are clearly visible in the LowZ/XVI image highlighting the superior contrast and preservation of spatial resolution.

Practical Embodiment

FIGS. 10 to 13 show a practical version of an Elekta treatment head incorporating the above ideas. They show part of the wall of a vacuum chamber 100 which incorporates an electron gun 102 (illustrated schematically) such as a linear accelerator. This wall 100 has an aperture 104 which is covered by a sliding carrier 106 that includes a Tungsten/Copper layered target 108 and an electron window 110. In one position, shown in FIG. 10, the carrier 106 is moved so that the target 108 covers the aperture 104. In another position, shown in FIG. 11, the carrier 106 is moved so that the electron window 110 covers the aperture 104.

Figure 14:
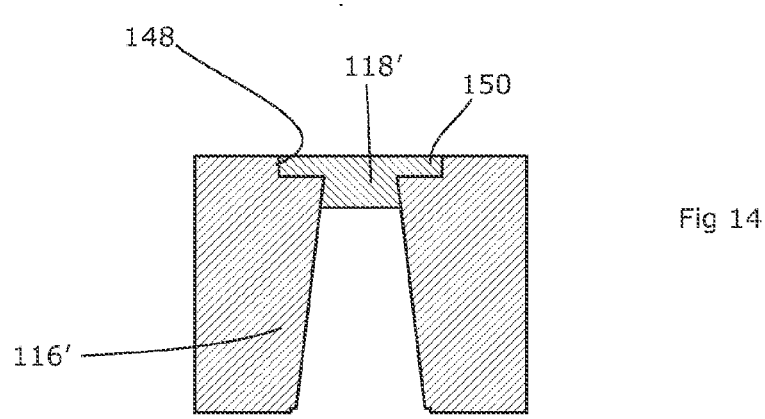

Immediately outside the chamber 100 is a primary collimator set 112. This set 112 includes a first primary collimator 114 and a second primary collimator 116 into which has been inserted a carbon absorber 118 held in place with Aluminium support struts 120. The carbon absorber 118 could of course be held in place by a variety of alternative means, such as by providing suitable recess. FIG. 14 shows such an arrangement, in which the primary collimator 116' is re-shaped to include a wider diameter recess 148 and the carbon filter 118' has a corresponding collar 150 so that it sits in the recess 148. The set 112 is indexable between two positions, akin to the sliding carrier 106, so that one primary collimator, of the two is presented in front of the aperture 104.

If required a diagnostic filter could also be placed close to (or attached to) the electron absorber to reduce the patient skin dose from low energy photons (<30 keV).

Beneath the primary collimator set 112, there is a motorised filter carousel 122. This is mounted on an axle 124 offset to one side beneath the aperture 106 and includes a plurality of filter recesses 126, 128. A first filter recess 126 is (in this case) empty although is could alternatively contain a conventional flattening filter. A second filter recess 128 contains a so-called "bow-tie" filter 130. Bowtie filters are used in CT (computed tomography) scanning for a variety of reasons, including to equalise the signal to noise ratio and to eliminate certain image artifacts etc. Generally, a bow-tie filter is used to compensate the X-ray attenuation for the different thickness regions in the patient, so that uniform X-ray intensity is produced at the detector. It allows a greater intensity to pass in a central region of the beam, progressively attenuating the beam more towards the outer edges.

Below the bow-tie filter 130, there is an ion chamber 132 (FIG. 12) and a set of collimators generally indicated as 134. This can include elements such as multi-leaf collimators, block collimators, and the like, operating in one or more planes transverse to the beam.

Below the collimators there will usually be a patient 136 supported on a patient table 138. Below the patient table is a flat panel scintillator detector 140 (as described above), mounted on an automated imager arm (not shown) which can extend the flat panel detector 140 into place or withdraw it, as required.

Figure 13:
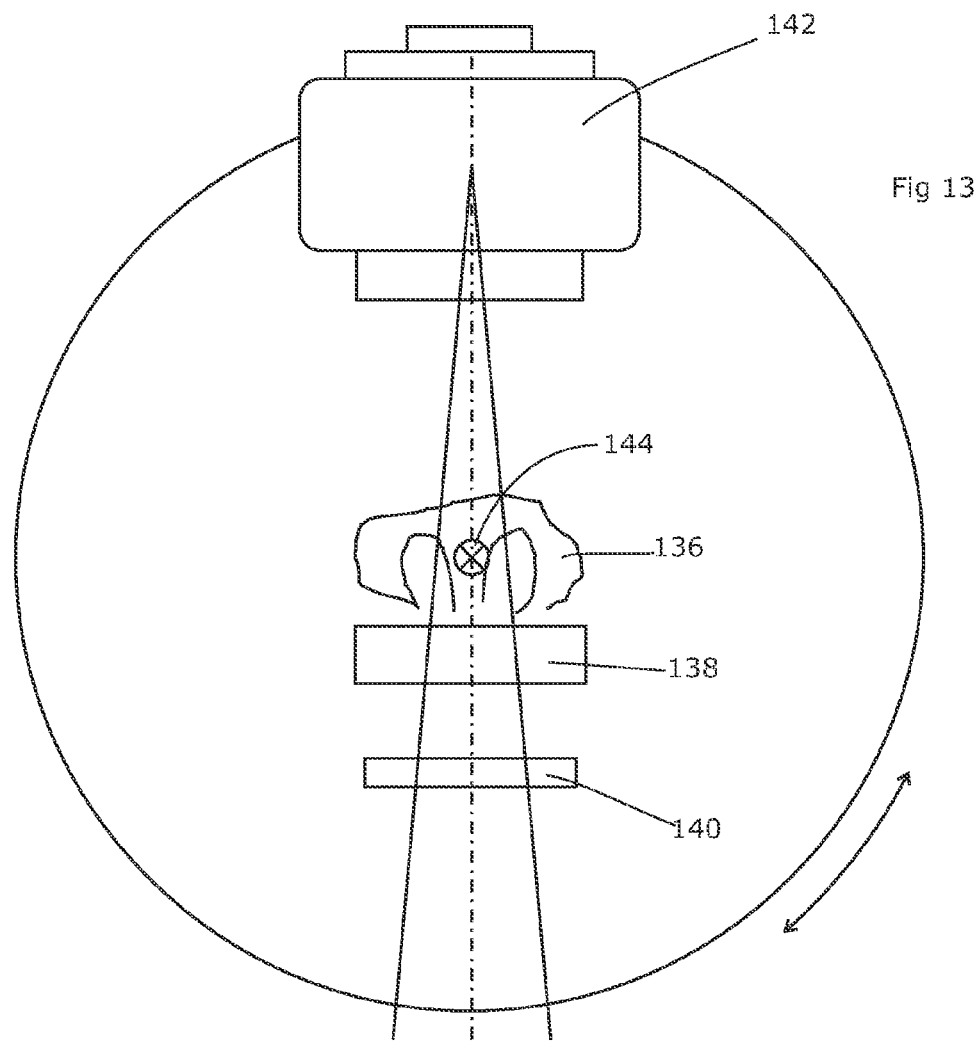
FIG. 13 shows the radiotherapy apparatus as a whole.

As shown in FIG. 13, the entire radiation head 142 is mounted so as to be rotatable around a horizontal axis 144, taking the flat panel detector 140 with it. The patient 136 is supported on the patient table 138 so that the axis 144 is within the patient. The intersection of the axis 144 with the centre of the beam produced by the radiation head 142 is usually referred to as the "isocentre". It is usual for the patient table 138 to be motorised so that the patient 136 can be positioned as required with the tumour site at or close to the isocentre.

Thus, the electron gun 102 creates an electron beam 146 which is directed towards the aperture 104. The first configuration to consider is that shown in FIG. 10, in which the Cu/W target 106 covers the aperture 104 and the empty primary collimator 114 is beneath the aperture, followed by the empty filter holder 126 (or a flattening filter). In this arrangement, the electron beam will impinge on the target 108 and create a therapeutic beam of x-rays. These will be roughly collimated by the primary collimator 114 and then (optionally) flattened before being collimated to a desired shape by the main collimator set 134. Thus, a normal x-ray treatment is obtained.

By moving the sliding carrier 106, the Cu/W target is moved out of the way of the electron beam and is replaced with the electron window 110. Provided that no other changes are made, the electron beam will then escape from the radiation head 142 and, after collimation, impinge on the patient. This mode is suitable for some treatments, particularly those involving the skin.

If the primary collimator set 112 is also moved, then the alternative primary collimator 116 will be employed and the carbon (preferably graphite) absorber 118 will be placed in the path 146 of the electron beam. This will absorb the electrons and prevent them from reaching the patient. As a result, the only significant emission of the radiation head 142 will be the bremsstrahlung created by interaction of the electron beam and the Nickel electron window, which will then be acting as a target. Of course, this bremsstrahlung radiation was also created while the apparatus was operating in the electron treatment mode, but was a very low dose compared to the electron beam.

The flat panel detector 140 can then be brought into the beam by extending the imager arm, to provide high contrast x-ray images of the patient using the low energy (kV) radiation produced by the radiation head 142. The motorised collimators 134, normally used for shaping the high energy (MV) therapeutic beam can then be used to shape the diagnostic beam. Thus, it is straightforward to automatically produce different imaging field sizes, removing the current need for different removable collimator cassettes in the kV beam.

Figure 11:
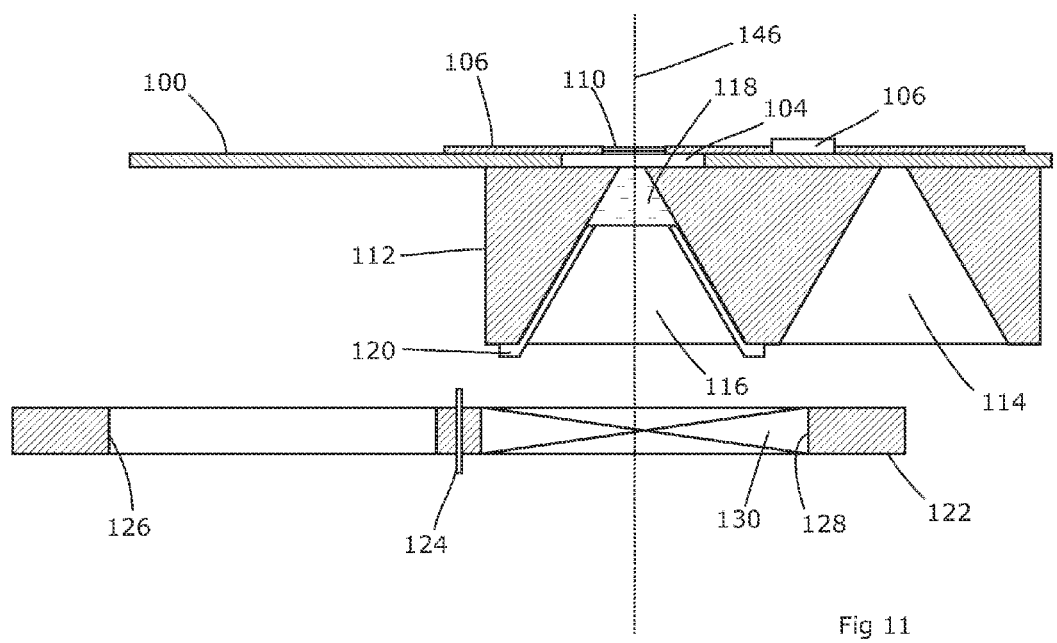
FIG. 11 shows the region around the target & primary collimator of the embodiment of FIG. 10, in a second arrangement.
Figure 12:
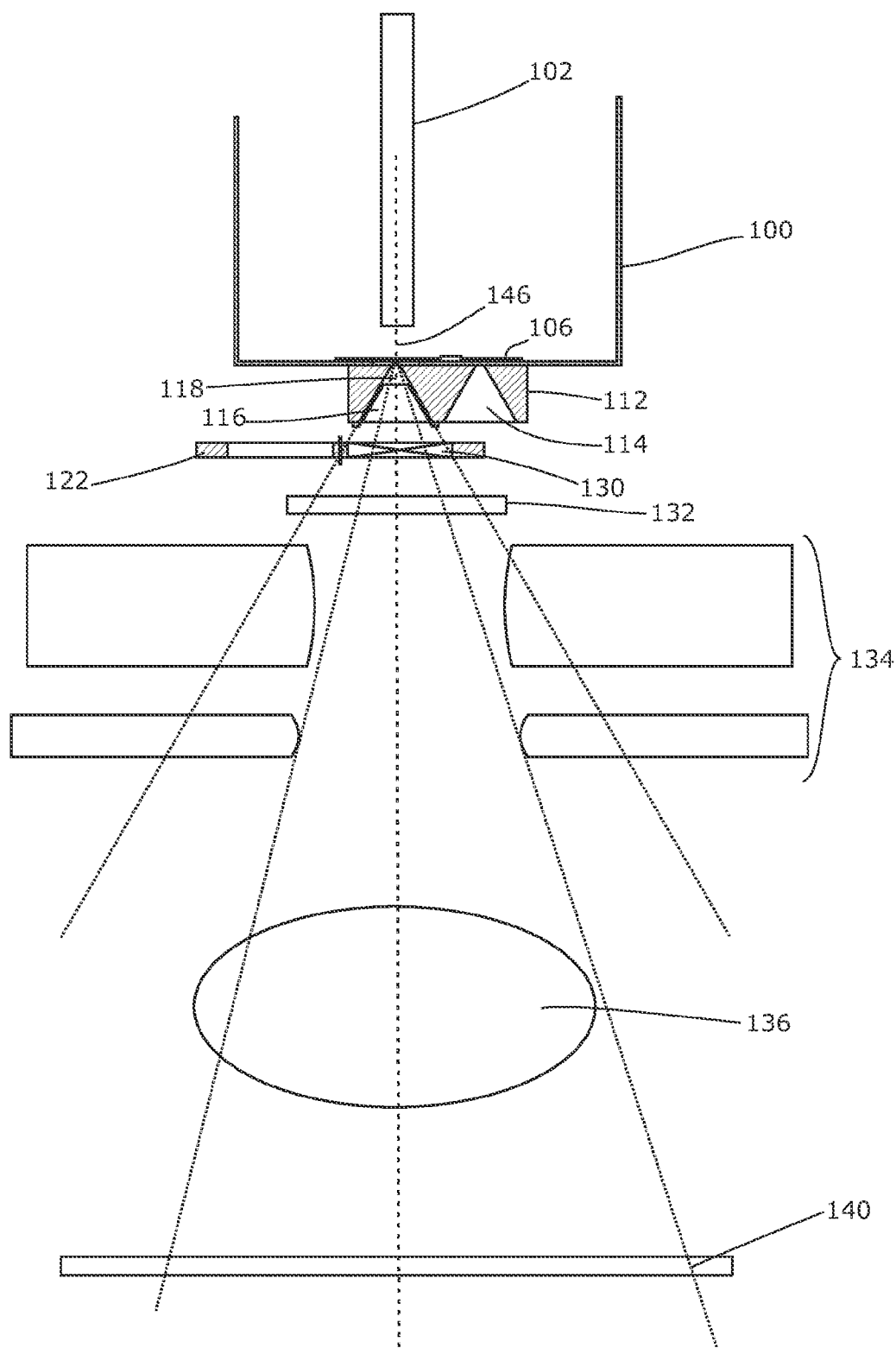
FIG. 12 shows the embodiment of FIG. 11 in context as part of a radiotherapy apparatus.

If the filter carousel is then also rotated in order to bring the bow-tie filter 130 into the path of the low-energy x-ray beam, to produce the arrangement shown in FIG. 11, then a beam that is highly optimal for cone beam CT scanning is obtained. The radiation head 142 and the flat panel detector 140 can be rotated around the patient 136 in order to obtain a good set of two-dimensional images for use in creating a cone beam CT image set.

CONCLUSION

A low Z system has been implemented that produces superior images than that of the current 6MV/iViewGT combinations. The use of a highly quantum efficient detector optimised for the KV energy range results in a contrast improvement of a factor of 4.62 for thin (5.8 cm thick) phantoms and 1.3 for thicker 25.8 cm phantoms. Most importantly, significant dose savings have been noted suggesting this technique would be well suited for megavoltage CT. Such systems have hitherto been limited by the large dose required to acquire the projection images.

The system offers a very simple modification to a standard linac coupled with a readily available imaging panel. Whilst the system is unlikely to compete with the dose and contrast results of gantry mounted kV systems, it offers a less complex solution and an image originating from the therapeutic portal of the linear accelerator. These advantages will, in practice, be more valuable.

It will of course be understood that many variations may be made to the above-described embodiment without departing from the scope of the present invention.

The invention claimed is:

1. A radiation source, comprising:
   an electron gun,
   a pair of targets each locatable in the path of a beam produced by the electron gun, the targets having different emission characteristics, wherein a first target of the pair is an electron window that emits x-radiation used for the production of images, and
   an electron absorber insertable into and withdrawable from the path of the beam for removing electrons from the beam but allowing x-radiation to pass through.

2. A radiation source according to claim 1, wherein the electron window is of Nickel.

3. A radiation source according to claim 1, wherein a second target of the pair is of Copper, Tungsten, or a composite including Copper and Tungsten.

4. A radiation source according to claim 1, wherein the electron absorber comprises a material of a lower atomic number than the electron window.

5. A radiation source according to claim 1, wherein the electron absorber is of Graphite, Carbon, Beryllium or Aluminium.

6. A radiation source according to claim 1, wherein the electron gun is within a vacuum chamber, and at least one of the targets is located at a boundary of the vacuum chamber.

7. A radiation source according to claim 1 further comprising:
   a primary collimator located in the beam subsequent to the targets.

8. A radiation source according to claim 7, wherein the electron absorber is located in the primary collimator.

9. A radiation source according to claim 7, wherein there are a plurality of primary collimators interchangeably locatable in the path of the beam, at least one of which primary collimators contains the electron absorber.

10. A radiation source according claim 1, wherein the electron window is substantially transparent to the beam.

11. A radiation source according to claim 1 further comprising:
    at least one of a bow-tie filter and a diagnostic filter, such filter being selectably locatable in the path of the beam.

12. A radiation source according to claim 1 further comprising:
    at least one adjustable collimator extendable into the path of the beam thereby to delimit it, the adjustable collimator being sized to substantially attenuate a megavoltage x-ray beam.

13. A radiotherapy apparatus including a radiation source according to claim 1.

14. A radiotherapy apparatus according to claim 13, wherein the radiation source is rotatable around a horizontal axis that lies in the path of the beam.

15. A radiotherapy apparatus according to claim 14, wherein the horizontal axis is perpendicular to the beam.

16. A radiotherapy apparatus according to claim 13, further comprising a flat panel imaging device in the path of the beam.

17. A radiotherapy apparatus according to claim 16, wherein the flat panel imaging device includes a scintillator layer.

18. A radiotherapy apparatus according to claim 17, wherein the scintillator layer includes of at least one of Caesium Iodide, Gadolinium Oxisulphide and Cadmium Tungstate.

19. A radiotherapy apparatus according to claim 13, further comprising a patient support between the source and the flat panel imaging device.

20. A radiotherapy apparatus according to claim 13 further comprising:

a control means programmed to obtain a plurality of two-dimensional images using x-radiation produced by the radiation source, and a reconstruction means adapted to reconstruct those images to form a three-dimensional CT dataset.

* * * * *

UNITED STATES PATENT AND TRADEMARK OFFICE
CERTIFICATE OF CORRECTION

PATENT NO.       : 8,355,482 B2                                              Page 1 of 1
APPLICATION NO. : 12/992727
DATED            : January 15, 2013
INVENTOR(S)      : Brown et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 131 days.

Signed and Sealed this
First Day of September, 2015

Michelle K. Lee
*Director of the United States Patent and Trademark Office*